(12) United States Patent
Üstüner et al.

(10) Patent No.: US 6,780,152 B2
(45) Date of Patent: Aug. 24, 2004

(54) METHOD AND APPARATUS FOR ULTRASOUND IMAGING OF THE HEART

(75) Inventors: Kutay F. Üstüner, Mountain View, CA (US); Thilaka S. Sumanaweera, Los Altos, CA (US); Sevig Ayter, Cupertino, CA (US); Kenneth M. Fowkes, Mountain View, CA (US); John A. Hossack, Charlottesville, VA (US); John W. Allison, Los Altos, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 10/180,386

(22) Filed: Jun. 26, 2002

(65) Prior Publication Data

US 2004/0006266 A1 Jan. 8, 2004

(51) Int. Cl.[7] ................................................. A61B 8/00
(52) U.S. Cl. ...................................................... 600/443
(58) Field of Search ................................ 600/437–471; 73/625, 626; 367/7, 11, 130, 134, 97; 128/916

(56) References Cited

U.S. PATENT DOCUMENTS

| | | | | |
|---|---|---|---|---|
| 4,159,462 A | * | 6/1979 | Rocha et al. | 367/97 |
| 4,254,662 A | * | 3/1981 | Kuroda et al. | 73/626 |
| 4,319,489 A | * | 3/1982 | Yamaguchi et al. | 73/626 |
| 5,908,390 A | * | 6/1999 | Matsushima | 600/447 |
| 5,961,460 A | | 10/1999 | Guracar et al. | |
| 6,014,473 A | | 1/2000 | Hossack et al. | |
| 6,048,316 A | | 4/2000 | Zhao et al. | |
| 6,120,453 A | | 9/2000 | Sharp | |
| 6,193,663 B1 | | 2/2001 | Napolitano et al. | |
| 6,352,508 B1 | | 3/2002 | Pang et al. | |
| 6,364,835 B1 | | 4/2002 | Hossack et al. | |

OTHER PUBLICATIONS

"Quantitative Three–Dimensional Echocardiography by Rapid Imaging from Multiple Transthoracic Windows: In Vitro Validation and Initial In Vivo Studies," by Daniel F. Leotta, MS, Brad Munt, MD, Edward L. Bolson, MS, Carol Kraft, RDCS Roy W. Martin, PhD, Catherine M. Otto, MD, and Florence H. Sheehan, MD, Seattle, Washington; Journal of the American Society of Echocardiography, Oct. 1997, vol. 10, No. 8, pp. 830–839.

* cited by examiner

*Primary Examiner*—Ali Imam (57) ABSTRACT

Images of the heart are formed by using multiple sets of ultrasound data. Each set of data is acquired and processed responsive to a different set of imaging parameters. The imaging parameter sets differ in at least one parameter, such as array position, temporal frequency response or transmit focal depth, so that the images formed using these data sets have, either laterally or axially, different spatial spectra. A set of images is formed responsive to a first imaging parameter set for a first cardiac cycle. Another set of images is formed responsive to a second imaging parameter set for a second cardiac cycle. The two sets of images are temporally aligned so that they correspond to the same set of phases of the cardiac cycle. Since the data acquisition and processing are distributed over multiple cycles of the motion, assuming regular periodic heart cycle, temporal resolution is maintained.

51 Claims, 5 Drawing Sheets

METHOD AND APPARATUS FOR ULTRASOUND IMAGING OF THE HEART

BACKGROUND

The present invention relates to forming images of the heart from multiple sets of ultrasound data.

Ultrasound is widely used for cardiac imaging. The quality of cardiac ultrasound images is determined mainly by the size and acoustic transparency of the acoustic windows through which the heart can be imaged. The rib cage offers multiple spatially distinct acoustic windows, but each window has a small area. Therefore transducers used in Cardiology applications typically have small apertures, such as 19.2 millimeters×14 millimeters. As a result, the detail resolution and field of view are limited and the ability to detect directional targets, such as endocardial borders, is impaired. The limited access also means poor signal-to-noise ratio (SNR). The poor SNR may particularly impact those modes that inherently have low SNR, such as the harmonic imaging. During the course of an ultrasound cardiac exam, a transducer is scanned across the rib cage to image from various spatially separated acoustic windows. The images from different acoustic windows are viewed separately. Therefore, information content determined by the field of view, detail and contrast resolution and SNR is limited by the individual acoustic window size and quality.

Another important factor that determines the quality of cardiac ultrasound imaging is the frame rate. Valves and other quickly moving objects within a heart may be poorly imaged due to insufficiently low frame rates. Therefore techniques that require multiple firings per beam such as certain types of compounding and sequential focus are typically not used for cardiac ultrasound.

Three-dimensional cardiac imaging has also been provided. Leotta et al. provide for three-dimensional cardiac imaging using multiple transthoraxic acoustic windows as described in "Quantitative three-dimensional echocardiography by rapid imaging from multiple transthoraxic windows: in vitro validation and initial in vivo studies," Journal of the American Society of Echocardiography, Vol. 10, No. 8, pp. 830–839 (1997). A two-dimensional image of the heart is acquired through each of multiple transthoracic windows. Regions or 3-D surfaces within each image are detected. Using magnetic positions sensors on a transducer, the relative position of each of the borders to other detected borders is used to generate a surface. The surface is then rendered in two dimensions for display to the user.

Other techniques for combining ultrasound images are known. U.S. Pat. No. 6,014,473 discloses compounding detected images associated with different transducer array positions to form an extended field of view. Images associated with different array or aperture positions may also be combined prior to detection. Spatial compounding may also be provided combining images associated with steering scan lines at different angles to a stationary array. The technique of combining images from different acoustic windows before the amplitude detection is known as the synthetic aperture, while combining such images post-detection is known as spatial compounding or compound aperture. The synthetic aperture reduces the size of speckle, which is the image of irresolvable targets, and increases the detail resolution of resolvable targets. The compound aperture, on the other hand, reduces the variance of speckle and improves detectability of directional targets U.S. Pat. Nos. 6,132,374 and 6,048,316 discloses sequential focus or compounding images associated with different focal depths. U.S. Pat. No. 5,961,460 discloses compounding images associated with different center frequencies. There is a need for ways to apply these techniques to imaging a dynamic object like heart, which is accessible from multiple spatially distinct acoustic windows.

BRIEF SUMMARY

The present invention describes forming images of the heart by acquiring and processing multiple sets of ultrasound data where each set is responsive to a different set of imaging parameters. The imaging parameter sets differ in at least one parameter, such as array position, temporal frequency response or transmit focal depth, so that the images formed using these data sets have, either laterally or axially, different spatial spectra. The multiple images thus formed are combined to improve contrast resolution and field of view.

In one aspect, a set of images is formed responsive to a first imaging parameter set for a first cardiac cycle. Then another set of images is formed responsive to a second imaging parameter set for a second cardiac cycle. Alternatively, the two sets of images are formed for a sub-cycle of interest, rather than for a full cardiac cycle, using first and second cardiac cycles. Then, the two sets of images are temporally aligned so that they correspond to the same set of phases of the cardiac cycle. The temporally aligned images may also be spatially aligned and combined.

One of the imaging parameters of interest that is varied between the two data acquisition events is the array position. Combining images of anatomical structures common to spatially distinct array positions can improve the contrast resolution, and/or assembling (e.g. volume rendering) the images of anatomical structures uncommon to the different array positions can extend the field (e.g. volume or area) of view. In one of the embodiments, the multiple data sets are acquired sequentially by acquiring a first set from an acoustic window, manually translating the transducer across an acoustically opaque barrier such as a rib, acquiring a second set and so on. The translation is done such that the imaging plane is substantially preserved. In another embodiment, a transducer with multiple spatially distinct coplanar arrays is used to acquire the multiple data sets. To get the benefit of spatial compounding the multiple arrays are arranged such that their imaging planes are the same, or, in the case where each array is a 2-D array, at least one of the imaging planes is common to both arrays. The separation and relative angle of these arrays may be adjustable to accommodate patient-to-patient and view-to-view variations of the acoustic window position and angles.

Forming an image by combining multiple images where each image is responsive to a different array position requires spatial alignment of the images prior to combining. Since the heart is dynamic, the sets of images are also temporally aligned prior to combining. Therefore, methods of spatial and temporal alignment of the multiple images are also described.

Another imaging parameter of interest that is varied between the two data acquisition events is the imaging center frequency. Combining images at different imaging center frequencies (e.g. frequency compounding) improves contrast resolution by reducing speckle variance. Yet another imaging parameter of interest is transmit focal depth. Combining images responsive to different transmit focal depths (e.g. sequential focus), extends the depth of field.

Improved images of objects associated with cyclical motion are provided without sacrificing temporal resolution by distributing the processing required for techniques such as frequency compounding, spatial compounding or sequential focus over multiple cycles of the motion. These methods and systems are applicable to 2-D or 3-D imaging of any dynamic object with cyclic motion, and/or objects that offer multiple spatially separated acoustic windows.

The present invention is defined by the following claims, and nothing in this section should be taken as a limitation on those claims. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Methods and systems for forming images of the heart by using multiple sets of ultrasound data are described. Each set of data is acquired and processed responsive to a different set of imaging parameters. The imaging parameter sets differ in at least one parameter, such as array position, temporal frequency response or transmit focal depth, so that the images formed using these data sets have, either laterally or axially, different spatial spectra. In one of the preferred embodiments, a set of images is formed responsive to a first imaging parameter set for a first cardiac cycle. Another set of images is formed responsive to a second imaging parameter set for a second cardiac cycle. Then, the two sets of images are temporally aligned so that images in the sets of images correspond to the same set of phases of the cardiac cycle. The temporally aligned images are also spatially aligned and combined if associated with different areas (e.g. transducer or aperture differences). This technique can improve contrast resolution and/or the field of view. Since the data acquisition and processing are distributed over multiple cycles of the motion, assuming regular periodic heart cycle, temporal resolution is maintained. The methods and systems described here can in general be used for imaging dynamic objects with cyclic motion, and/or objects that offer multiple spatially separated acoustic windows.

Figure 1:
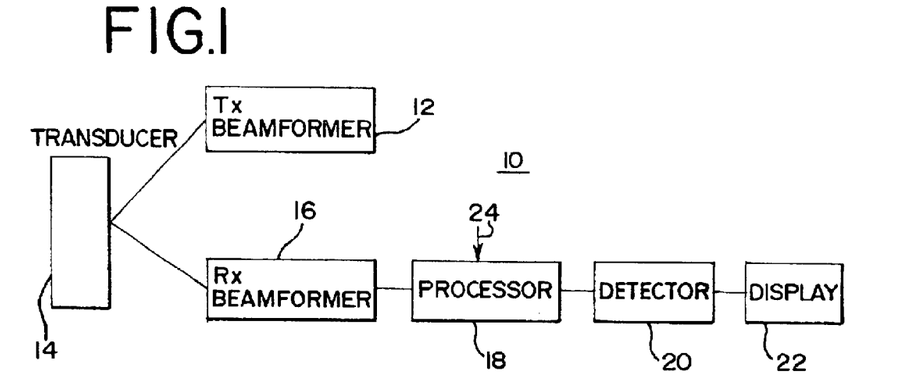
FIG. 1 is a block diagram of an ultrasound system of one embodiment for acquiring data for imaging an object.

FIG. 1 shows an ultrasound system 10 for acquiring cardiac images of the heart. The system 10 includes a transmit beamformer 12, a transducer 14, a receive beamformer 16, one or more processors 18, a detector 20 and a display 22 operationally connected as shown. Additional, fewer or different components may be provided.

The transmit beamformer 12 comprises analog and/or digital components for generating a plurality of respectively delayed and apodized waveforms. The waveforms are associated with a spectral response or spectrum. For example, a center frequency of 3 Megahertz or another value is provided. By varying the center frequency, focal depth, and the steering angle or other waveform characteristic, images with different spatial spectra are provided. For example, the steering angle or origin of a transmit beam responsive to the transmit waveforms is associated with a particular bandwidth. By varying the position, size or spacing of the transmit aperture, a different spectral response is provided.

The transducer 14 comprises an array of piezoelectric or microelectromechanical transducer elements. The elements are arrayed as a one-dimensional linear, curved linear or other array. 1.5 and 2-dimensional arrays may be provided. Arrays of small sizes, such as 19 millimeters by 12 millimeters may be used, and arrays of larger sizes may be used. In one embodiment, the transducer 14 is adapted for hand-held use external to a patient. For example, the transducer is adapted for use external to a patient where the elements are positioned adjacent to the ribs of the patient for cardiac imaging. Alternatively, a trans-esophageal or other probe for internal use is provided. The transducer 14 may or may not include a magnetic position sensor or other position sensor for determining a position and orientation of the transducer 14 relative to a patient.

Figure 6A:
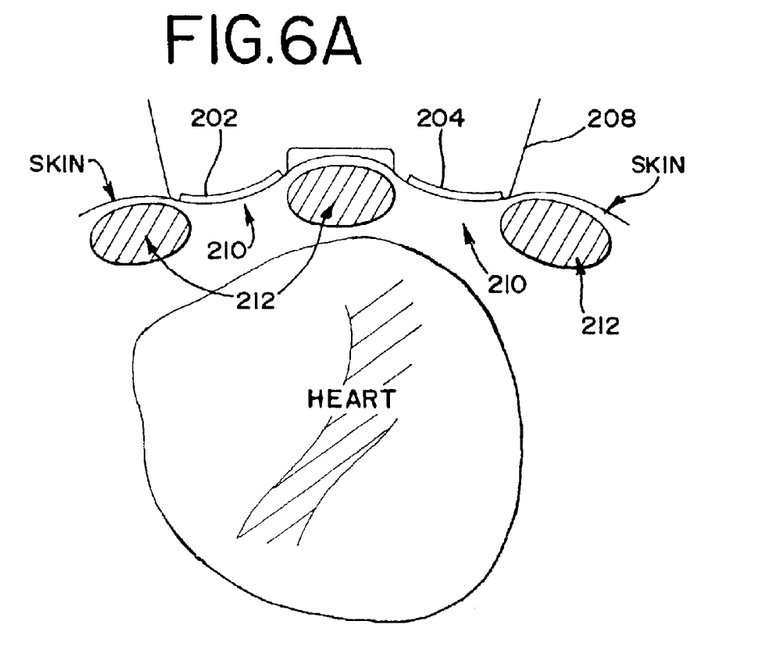
FIGS. 6A and 6B are a graphical representation of a transducer with coplanar arrays.
Figure 6B:
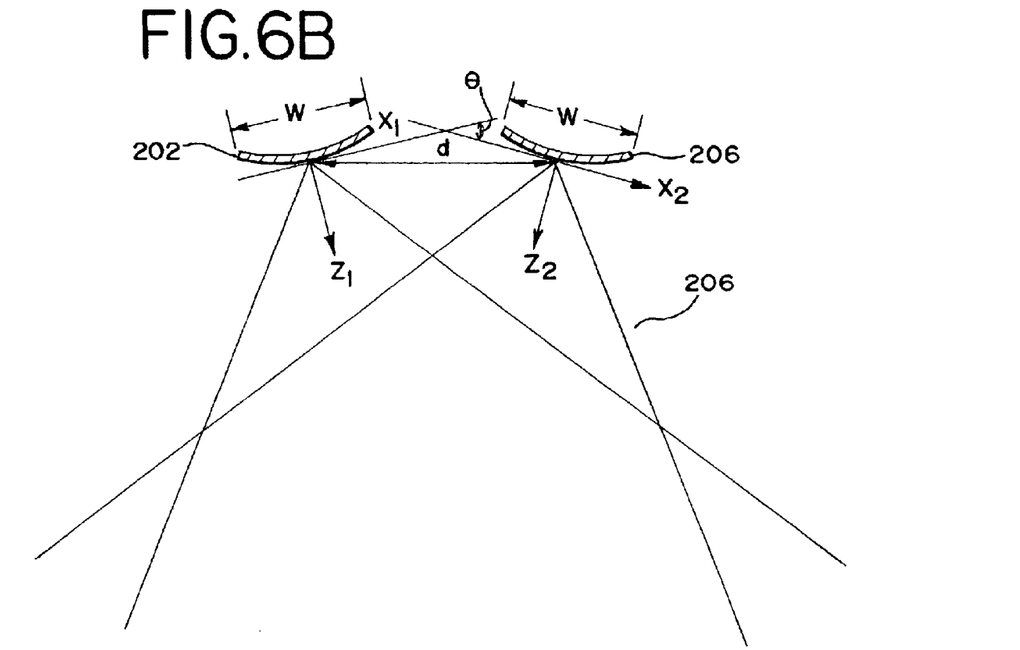

In one embodiment, the transducer 14 is adapted for use in imaging through two different acoustic windows separated by an opaque barrier without translation or other movement of the transducer 14. For example, a hand-held transducer 14 includes two arrays positioned apart so that one array is associated with a likely location of an acoustic window and the other array is associated with a likely location of a different acoustic window. The arrays are arranged such that their imaging planes are the same, i.e., they are coplanar, but may be arranged at other relative angles. FIGS. 6A and 6B show two coplanar arrays 202, 204. Their azimuth ($x_1$ and $x_2$) and range ($z_1$ and $z_2$) axes are in the same plane, i.e. the arrays 202, 204 share a common imaging plane 206. In the case of 2-D arrays, the arrays are spatially arranged such that there is overlap between the two acquired volume data sets. In other cases, there may not be an overlap.

A distance (d) that is equal to the average or desired rib spacing separates the arrays 202, 204, and the average relative angle of the two adjacent acoustic windows determines the relative angle ($\theta$) of the arrays 202, 204. Alternatively, d and/or $\theta$ are user adjustable to accommodate the patient-to-patient and view-to-view variability of the acoustic window separation and angle. In an alternative embodiment, the angle $\theta_1$ and $\theta_2$ of the arrays are independently adjustable.

Adjustable array separation allows forming an almost continuous aperture in those cases where there are large enough acoustic windows to accommodate both arrays 202, 204. If the arrays are close to each other, i.e., if d<2W, where the W is the width or azimuth extent of the arrays, then, in addition to incoherent techniques such as compound aperture, coherent techniques such as synthetic aperture may be used. Note that, while incoherent techniques increase contrast resolution through reducing speckle variance and increasing the detectability of directional targets, coherent techniques increase detail resolution. If the arrays 202, 204 are close to each other, one of the arrays 202 transmits acoustic energy and both arrays 202, 204 receive responsive echoes, and then the other array 204 transmits acoustic energy and both arrays 202, 204 receive responsive echoes. Each array applies appropriate delays with compensating terms for their positions and angles relative to the beam(s) to be formed. Then the delayed, apodized and summed outputs of the arrays are summed coherently (i.e. summed prior to amplitude detection), synthesizing an aperture that is larger than the aperture of individual arrays 202, 204. Alternatively, both arrays 202, 204 transmit acoustic energy simultaneously with appropriate delays compensating for the relative positions of the arrays 202, 204. The received echoes responsive to both transmissions are effectively delayed and summed by each array 202, 204 with appropriate delay compensations for the relative array positions. The signals output by the arrays 202, 204 are then summed coherently. Either with the former sequential firing synthetic aperture technique, or with the later single firing technique, a spatial spectrum that has a lateral bandwidth more than twice the bandwidth of the individual arrays is synthesized. If the separation between the two arrays 202, 204 is small, a continuous smooth spectrum without gaps in the pass-band is provided. As a result, a high resolution spatial response with low side lobes may be achieved within the transmit depth of field.

Using a transducer 208 with multiple spatially distinct coplanar arrays 202, 204, a compound aperture is formed by: generating a first set of amplitude detected images sampled during a first heart cycle using the first array; generating a second set of amplitude detected images sampled during a second heart cycle using the second array; spatially aligning the second set of images with the first set by applying a preset, measured or estimated array separation and angle information; phase aligning (i.e. temporally aligning) the second set of images with the first set of images by (a) resampling the second set of images at the same phases of the heart cycle as the first set of images in response to a cross correlation calculation or (b) acquiring the images with triggering using an ECG signal; and combining the spatially aligned and phase-aligned images. The combination is performed in the amplitude, intensity or log-compressed domains. The images are averaged, weighted and summed based on the pixel SNR ratio (e.g., SNR of the first array divided by the SNR of the second array, etc.), local SNR ratio, pixel coherence factor ratio or the local coherence factor ratio. Images can also be combined using the techniques described in U.S. Pat. No. 6,713,239.

The above method corresponds to heart-cycle interleaved acquisition of the two sets of images. The acquisition can alternatively be frame- or beam-interleaved.

If the arrays 202, 204 are user adjustable for d and/or θ, a lock mechanism prevents adjustments during the data acquisition. The lock reduces the risk of spatial misalignment of the images generated by the individual arrays 202, 204. The lock is enabled and disabled by the user or automatically. Further, if d and/or θ are adjustable, a mechanical, electronic, or electromagnetic sensor provides the imaging system information on d and θ or the relative position,of the arrays 202, 204. Alternatively, the position and angle are determined automatically by cross correlation of the images generated by the arrays 202, 204, assuming the field of views overlap. The coherent combination techniques, such as synthetic aperture, may use more accurate measurements or estimations of d and θ than the incoherent compounding techniques.

To maximize the acoustic coupling and patient comfort, each array 202, 204 has a footprint similar to a conventional cardiac transducer. Each array 202, 204 has a slightly curved convex geometry, but other geometries may be used. The curved array geometry may provide fields of view with more overlap so that arrays with fixed relative positions may be used. In one embodiment, the arrays 202, 204 are finely sampled, i.e., the arrays 202, 204 have small element pitch, such as $\lambda/2$, where $\lambda$ is the wavelength. Small element pitch allows for vector® or sector scan geometry, providing increased overlap of the fields of view. Compounding or synthesis of the images in an overlapping area of the field of view of the two arrays reduces speckle or increases resolution. The non-overlapping areas widen the composite field of view.

In another embodiment, the two or more views of an object, such as the heart, are acquired through different acoustic windows 210 by moving the transducer between the two acquisitions. Opaque barriers may separate the different acoustic windows, such as when imaging through different rib spaces. Opaque barriers close to the skin of a patient, such as the ribs 212 or other bone structures, interfere with imaging the heart or other organ. Opaque barriers may also not separate the different acoustic windows, such as when imaging through the same rib space.

The receive beamformer 16 comprises analog or digital components for generating data responsive to acoustic echo signals from the transmitted acoustic energy. The receive beamformer 16 applies relative delays and apodization to electrical waveforms generated by the elements of the transducer 14. The delayed and apodized waveforms are summed, providing data representing a receive beam or scan line. By applying various apodizations and delays with the transmit beamformer 12 and receive beamformer 16, multiple scan lines are sequentially and/or simultaneously scanned to generate a frame of data representing a two-dimensional region or image. For example, linear, sector or Vector® scan formats provide a field of view.

The data output by the receive beamformer 16 has a spectral characteristic. The spatial spectra of images formed from the data is responsive to a receive aperture, such as the number of elements, the spacing between elements used or the position of the aperture within the transducer 14. A filter may be provided in the receive beamformer 16 for operating at a particular frequency, such as the center frequency associated with the fundamental transmit frequency used by the transmit beamformer 12 or a harmonic of the fundamental transmit frequency. The spectrum associated with the received data is also controlled by the bandwidth of the filter, and the apodization applied by the receive beamformer 16. Other characteristics may be controlled by the receive beamformer for changing an imaging parameter or spectral characteristic of receive data.

The processor 24 comprises one or more of an application specific integrated circuit, a digital signal processor, a general processor, digital hardware, analog hardware and/or combinations thereof for processing the data output by the receive beamformer 16. The processor may comprise two or more separate processors for performing different functions or parallel functions. First and second processors are used herein to represent either of a same or different processor. The processor 18 receives an image or data representing a scan line from the receive beamformer 16. For data representing a scan line, the data is stored until an image frame or partial image is obtained. As used herein, image includes frames of data prior to scan conversion and image data after scan conversion. For example, frames of data prior to scan conversion may be temporally aligned using ECG triggering for dynamically imaging the heart, and scan converted images are spatially aligned. As another example, images prior to scan conversion or detection are spatially aligned in the polar coordinate domain. The processor 18 receives a first image and a second subsequent image.

The first image and other images are stored in a memory for selective synchronization. Where two images are responsive to different acoustic windows separated by an opaque barrier, the processor 18 spatially aligns the images, such as by correlating the first image with the second image. Where two images are associated with a physiological cycle, the processor 18 temporally aligns the images so that the selected first and second images are associated with the same phase of the physiological cycle. The processor 18 combines the spatially and temporally aligned images. The combined data represents an extended field of view, a same field of view or a three-dimensional field of view. Temporally aligned cardiac images from different cardiac cycles are combined using spatial compounding, compound aperture, synthetic aperture, sequential focus or compounding images associated with different center frequencies.

For temporal alignment, an ECG input 24 may be provided to the processor 18 or elsewhere in the system 10. The ECG input 24 is adapted for connecting with an ECG device for monitoring a heart cycle. In alternative embodiments, the ECG input 24 comprises an input for other physiological cycle measurement devices, such as a device for measuring a breathing cycle.

The detector 20 comprises a B-mode detector, a Doppler detector or other detector of a characteristic associated with the images. For example, the detector 20 detects an envelope magnitude, a velocity, a frequency, an energy, a variance or other characteristic for the images. As shown, the detector 20 is positioned to receive combined data from the processor 18. In alternative embodiments, the detector 20 is positioned before the processor 18 for detecting prior to combination. For combination prior to detection, in-phase and quadrature data is combined with or without phase alignment such as disclosed in U.S. Pat. No. 5,667,373, the disclosure of which is incorporated herein by reference.

In one embodiment, a filter is provided in the detector 20, the processor 18 or the receive beamformer 16. The filter is a digital or analog filter, such as a programmable digital filter. The finite impulse response or infinite impulse response of the filter is programmable, such as programming the number of taps or the weightings associated with any taps. The spectral response is programmable as a function of selected weightings and taps. In alternative embodiments, the filter provides a non-linear response, such as associated with application of velocity thresholds to energy data after detection in the detector 20. Other non-linear filters may be provided. In one embodiment, the filter comprises a clutter filter for removing information associated with slow or fast moving fluid or tissue, such as used for cardiac imaging. In another embodiment, the filter comprises an anti-aliasing filter. The linear or non-linear response, taps, weightings or other filter variable comprises an imaging parameter.

The display 22 comprises a monitor or other device for generating an image as a function of the combined images. The image is responsive to the imaging parameters used for acquiring the component images. By temporally and/or spatially aligning images responsive to different acoustic windows or different imaging parameters, high quality cardiac imaging may be provided. The image comprises an extended field of view image, such as associated with combining partially overlapping substantially coplanar images. In another embodiment, a two-dimensional image is associated with combining images representing a same or substantially same field of view. In yet other embodiments, a two-dimensional representation by combining or rendering from three-dimensionally spaced images is provided.

Figure 2:
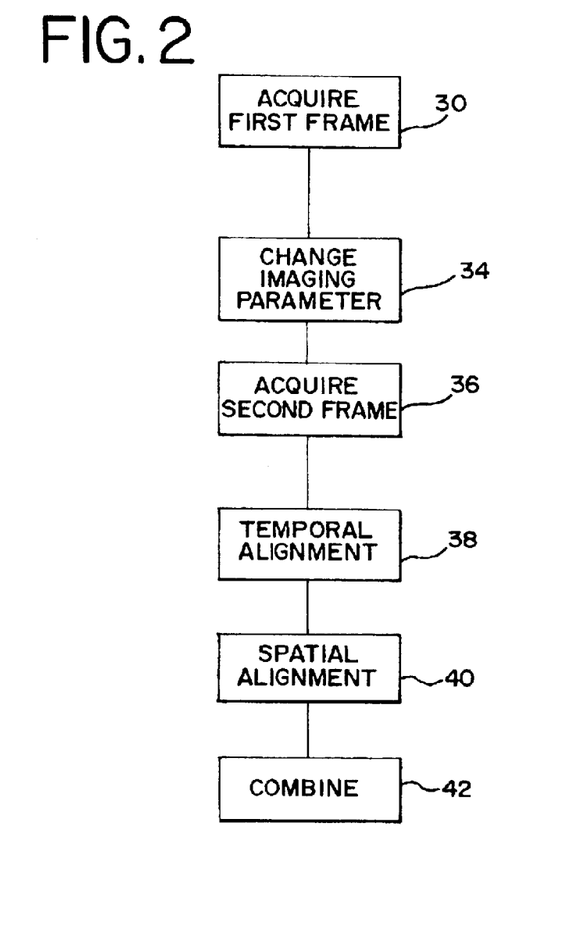
FIG. 2 is a flow chart diagram of one embodiment of a process for acquiring data for imaging an object.

FIG. 2 is a flow chart of a process for acquiring data for imaging a dynamic and/or partially obscured object, such as the heart. Two sets of images are acquired in acts 30 and 36. The sets of images are processed responsive to a different set of imaging parameters based on act 34. The imaging parameter sets differ in at least one parameter, such as array position, temporal frequency response or transmit focal depth, so that the images formed using these data sets have either laterally or axially different spatial spectra. In one embodiment, a set of images is formed responsive to a first imaging parameter set for a first full or partial cardiac cycle in act 30. Another set of images is formed responsive to a second imaging parameter set for a second full or partial cardiac cycle in act 36. Then, the two sets of images are temporally aligned so that images in the sets of images correspond to the same set of phases of the cardiac cycle in act 38. The temporally aligned images are also spatially aligned in act 40 if associated with different fields of view. The temporally and spatially aligned images are combined in act 42. This technique can improve contrast resolution and/or the field of view. Since the data acquisition and processing are distributed over multiple cycles of the motion, assuming regular periodic heart cycle, temporal resolution is maintained. The methods and systems described here can in general be used for imaging dynamic objects with cyclic motion, and/or objects that offer multiple spatially separated acoustic windows. Additional acts may be provided.

When the images are combined, imaging with reduced speckle variance is provided. Furthermore, depending on the position of the two different views, the field of view may also be wider than that is normally possible with a conventional probe. Changing the spatial characteristic, results in more comprehensive views of areas obscured by opaque barriers. Changing the temporal and/or imaging parameter characteristics may provide improved images of objects associated with dynamic motion without sacrificing temporal resolution.

In acts 30 and 36, first and second sets of images are acquired. Each set of images is associated with an acoustic window. In one embodiment, the acoustic window is defined by one or more opaque barriers limiting access of ultrasound energy from the transducer 14 to a region of interest, such as ribs of the patient being imaged. In other embodiments, the acoustic window is defined by the position of the transducer 14 without limitation by an opaque barrier. For example, the transducer is positioned on one portion of a patient defining a first acoustic window and repositioned on a different portion of the patient, defining a second acoustic window within a same rib space.

Where a dynamic or moving object responsive to a physiological cycle is insonified, each image is associated with a phase of the physiological cycle. For example, an image is acquired at an R wave portion of a heart cycle. The images are temporally labeled by registration with an ECG signal or other signal indicating the phase of the physiological cycle. Where the images are sequentially acquired, the images may be associated with a same or different phase of subsequent physiological cycles.

One set of images is acquired by repetitively scanning a field of view over a portion of a physiological cycle, over an entire physiological cycle, or over multiple physiological cycles. In alternative embodiment, a set of images corresponds to an arbitrary or other triggering parameter, such as imaging for a period of time of a non-dynamic object. The first set of images, including a first image, is responsive to one acoustic window and one set of imaging parameters. A second image associated with a second set of images is associated with a same or different acoustic windows and the same or different imaging parameters. The images within a set are each associated with different or repeating phases of the same or subsequent physiological cycle in one embodiment. In alternative embodiments, a physiological cycle is not tracked.

Figure 3A:
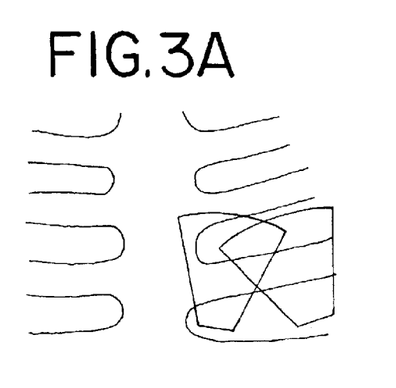
FIGS. 3A and 3B are graphical representations of acquiring data for imaging the heart through different acoustic windows.
Figure 3B:
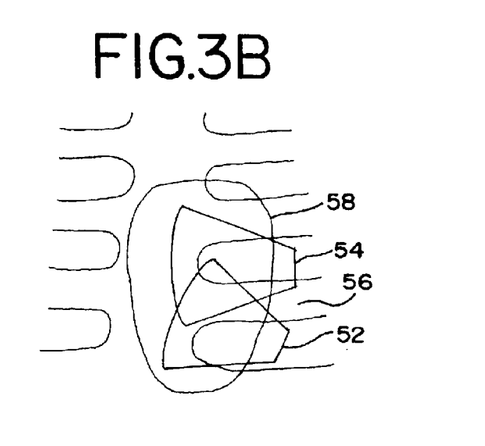

A spatial or temporal characteristic changes between acquisition of the first and second sets of images in acts 30 and 36. For changing a spatial characteristic, a different acoustic window is used. In one embodiment, the different acoustic windows are separated by an opaque barrier, such as gas, bone or other structure limiting propagation of ultrasound energy. FIG. 3B shows two fields of view 52 and 54 separated by the opaque barrier 56. The opaque barrier 56 comprises bone or a rib. The ribs define two different acoustic windows associated with the fields of view 52, 54 of the heart 58. By translating between or positioning at different acoustic windows, the combined field of view images partially overlapping areas of the heart 58. The heart 58 may be imaged through various intercoastal spaces or acoustic windows. In an alternative embodiment shown in FIG. 3A, the array is translated within the same rib space for acquiring the two sets of images.

In other embodiments, the circle of Willis or other portions of a head are scanned through different acoustic windows separated by a brain structure barrier. The circle of Willis, for example, can be imaged through two different windows: the right temporal bone window and the left temporal bone window. The kidney is imaged from the back and from the side of the abdomen separated by a fat barrier. Intercoastal and subcoastal acoustic windows are used for imaging the kidney as separated by gas or rib barriers. The lungs are imaged from the back and from the front of a patient, separated by bone barriers. As yet another example, the brain of a neonatal infant can be imaged though the fontanelle, the temporal bone, or the occipital opening, all of which are different acoustic windows separated by a bone structures. In yet another example, the ovaries or uterus are imaged through the abdomen exterior to a patient and through the vaginal cavity using an endovaginal transducer where the acoustic windows are separated by tissue, bone or gas. The opaque barrier separates the access to the same area.

In one embodiment, the images are acquired using different acoustic windows by mechanically translating and/or rotating a transducer from one acoustic window to another. Each acoustic window is used independently or without translation of the transducer over the opaque barrier while acquiring data. In an alternative embodiment, different transducers are used for each of the acoustic windows.

Where the sets of images are acquired during different cardiac cycles or at different times, a temporal characteristic is different for one set of images than for the other set of images. For example, each image is associated with a same phase of different physiological cycles. As another example, a second image is acquired subsequent to a first image. Where multiple images are provided within sets, images from each of the sets may be associated with the same portion or phase of the different physiological cycles.

In act 34, one or more imaging parameters are changed between acquiring the first and second sets of images. Changing the imaging parameter changes the spatial spectra associated with each of the images. For example, each image is acquired with a different operating frequency, such as with different transmit frequencies and/or different receive frequencies. The different center frequency associated with the transmit or receive operation results in a different spectrum for the first set of images than for the second set of images. In one embodiment, the first set of images are associated with receiving at a fundamental frequency or the same frequency as the transmit frequency. The second set of images are associated with receiving at a harmonic of the same fundamental or a different fundamental transmit frequency.

Other axial or lateral changes in the frequency spectrum may be provided. For example, the shape of the spectrum or bandwidth of the spectrum is different for each image, such as by providing a wide bandwidth and a narrow bandwidth. As another example, the focal depth (transmit delay profile) associated with one image is different than the focal depth associated with the second image. As an example of a lateral frequency shift, a transmit and/or receive aperture associated with the first image is different than the transmit or receive aperture associated with the second image. Different apertures are provided by using a different number (width), different spacing or different position of elements for transmit and/or receive operations. The bandwidth is controlled by the aperture width or other transmit or receive characteristics, causing a lateral shift and different center frequency. As yet another example, a filter response is different for the first set of images than for the second set of images. For example, a transmit filter envelope or a receive filter envelope is different. Other filter related imaging parameters include the bandwidth of the filter, the spectral shape of the filter, the type of filter, or other programmable parameters of a filter. Other imaging parameters may be different.

In act 38, images are temporally aligned. By selecting images associated with the same phase of the cardiac or other cycle from the sets of images, the imaged dynamic object is substantially stationary or in the same position for both images. This object-cycle interleaving distributes the processing required for the two images over two or more cycles.

The sets of images are temporally aligned as a function of the phase of the physiological cycle. Images from one set are temporally aligned with respective images from the second set. A first image is temporally aligned with a second image where both images represent substantially the same phase of the physiological cycle. The first image is temporally correlated with the second image and represents an object in the same position relative to the physiological cycle.

In one embodiment, temporal alignment is performed in response to an ECG signal. As images are acquired, a time stamp of the ECG signal is recorded. The images with the same time stamp or representing the same phase of the physiological cycle are selected as a function of the ECG signal or time stamp. In an alternative embodiment, the images are acquired in response to an ECG signal trigger.

Each image within a set is acquired at a specific or triggered phase of the physiological cycle. In yet another alternative embodiment, the physiological cycle information is extracted as a function of acoustic data. For example, the maximum Doppler flow velocity or energy is detected, such as by summing the energy levels of the color pixels of a Doppler image and then dividing by the number of color pixels to derive mean energy. The mean energy is tracked as a function of time to identify the physiological cycle. Specific phases are then associated with each of the images as a function of the mean energy. In this approach, it is preferable to use a fast acquisition rate for dissecting the maximum Doppler flow rate (such as 20 frames per second or higher). Regardless of the frame rate that is used for the purpose of detecting the Doppler flow maximum, a subset of all the frames may be used for generating an image. In alternative embodiments, Doppler velocity or variance is detected as a function of time to identify a physiological cycle. In alternative embodiments, no temporal alignment is provided.

In act 40, the first image is spatially aligned with the second image. The spatial alignment is performed as a function of tracking information, such as from transducer position tracking devices or from correlation of data. Where the images are assumed to be coplanar, spatial alignment is performed within two dimensions. The images are alternatively aligned within three-dimensional space, including some or no overlapping. The images are aligned as a function of the area represented by the data. In alternative embodiments, no spatial alignment is provided.

Figure 4:
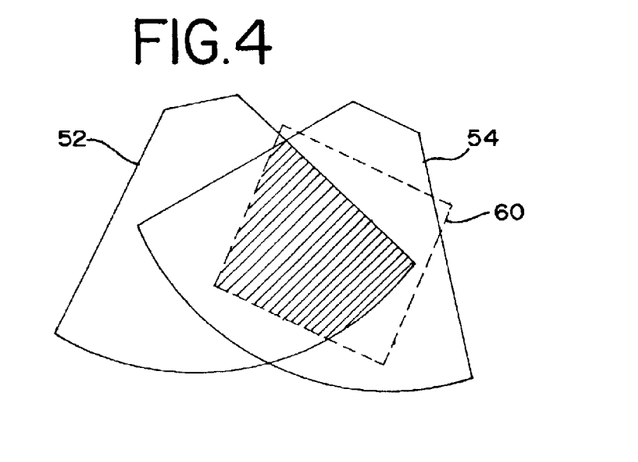
FIG. 4 is a graphic representation of a search area or correlation region for determining spatial alignment in a two-dimensional plane in one embodiment.

FIG. 4 shows one embodiment for spatially correlating a first image with a second image. In alternative embodiments, other correlation processes may be used, such as disclosed in U.S. Pat. No. 6,014,473, the disclosure of which is incorporated herein by reference. In FIG. 4, the first image associated with the field of view 52 is correlated with the second image associated with the field of view 54. Speckle, feature or other characteristics of the images are correlated. In one embodiment, features are identified within the images and correlated since acoustic windows separated by opaque barriers result in decorrelated speckle due to the distance between each field of view 52, 54.

Figure 7:
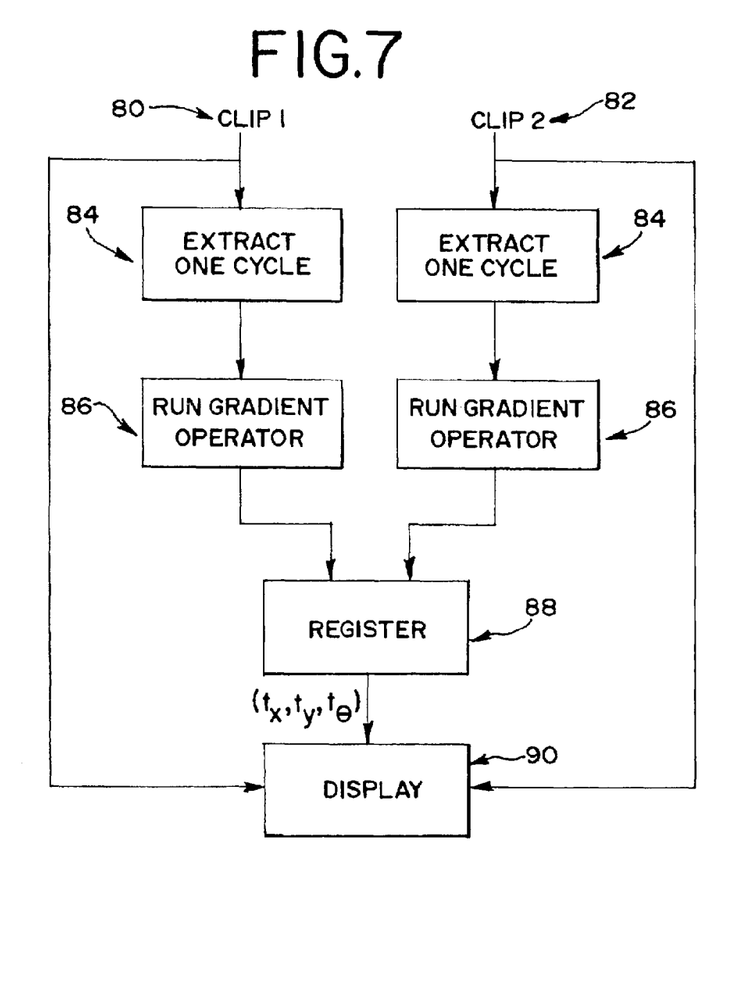
FIG. 7 is a flow chart diagram of one embodiment of a spatial registration.

FIG. 7 shows one embodiment for spatial alignment. Two sets of ultrasonic images, clip 1 (80) and clip 2 (82), corresponding to two different views of the heart, are obtained. The two views are assumed to be coplanar. During image acquisition, an ECG waveform is acquired for each clip. The two clips are assumed to be encapsulated in the DICOM format. Other forms for encapsulations, real time or non-real time, can also be used. The DICOM header contains flags referencing an acquisition time relative to a corresponding R-wave. In act 84, 2-D images corresponding to a single cycle in each clip are extracted. In the more general case, it is also possible to use all the cycles or all the images in each clip.

In act 86, a gradient operator is performed on the first image of each extracted cycle. The first image in each clip corresponds to the peak diastolic of the heart. In the more general case, the gradient operator may also run on additional or all of the images in each clip. Furthermore, the first image in each cycle may also correspond to a cardiac phase other than the peak diastolic of the heart. The gradient operator is given by Equations 1–5 below:

$$D_x(x, y) = \frac{-x}{2\pi\sigma_x^3\sigma_y} e^{-\frac{1}{2}\left[\frac{x^2}{\sigma_x^2} + \frac{y^2}{\sigma_y^2}\right]} \quad (1)$$

$$D_y(x, y) = \frac{-y}{2\pi\sigma_y^3\sigma_x} e^{-\frac{1}{2}\left[\frac{x^2}{\sigma_x^2} + \frac{y^2}{\sigma_y^2}\right]} \quad (2)$$

$$G_x(x, y) = D_x(x, y)^{**} I(x, y) \quad (3)$$

$$G_y(x, y) = D_y(x, y)^{**} I(x, y) \quad (4)$$

$$G_y(x, y) = \sqrt{G_x(x, y)^2 + G_y(x, y)^2} \quad (5)$$

Equations 1 and 2 show the x- and y-gradient kernels, $D_x$ and $D_y$, respectively. These kernels (a) smooth the image using a Gaussian kernel and (b) compute spatial derivatives. The quantities, $\sigma_x$ and $\sigma_y$, are the spreads of the Gaussian kernel. Equations 3 and 4 generate the intermediate derivative images, $G_x$ and $G_y$, respectively. $G_x$ corresponds to the spatial derivative with respect to x, while $G_y$ corresponds to the spatial derivative with respect to y. Equation 5 computes the gradient magnitude, G, from $G_x$ and $G_y$.

The gradient magnitude images from the two clips are then registered in act 88. The x- and y-translation, $t_x$ and $t_y$, and in-plane rotational translation, $t_\theta$, between the two gradient images are estimated. In the more general case, this computation may be performed for each pair of images corresponding to the same phase of the cardiac cycle. The computation may also be performed for one, two or more pairs of images corresponding to the same phase of the cardiac cycle. The two clips, 80 and 82, and ($t_x$, $t_y$, $t_\theta$) are displayed in act 90.

Figure 8:
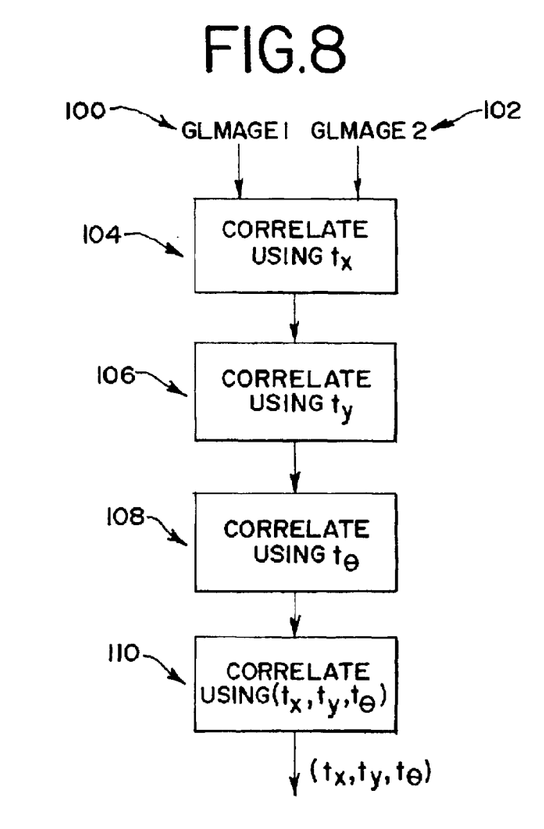
FIGS. 8 and 9 are flow chart diagrams of embodiments of a progressive correlation sequence.

FIG. 8 shows a more detailed process of the registration act 88. Registration is performed by cross-correlating a subset or all of the data in the two images. An image is typically 480 pixels high and 640 pixels wide. The subset of data may correspond to a rectangular region of 240 pixels high and 320 pixels wide area centered at the image. Regions with other shapes, such as a shape similar to a milk carton, a sector, a circle, an oval and other complex shapes, can also be used. Multiple regions may also be used.

The region from the gradient image, gImage1 (100), is translated and rotated for each point in the parameter space and a cost function is computed using the data from gImage1 (100) and gImage2 (102). The parameter space corresponds to the 3-dimensional space defined by x, y and θ. The cost function may include a correlation coefficient, a product of image intensities, a sum of absolute differences or any combination thereof To speed up computation, parallel processing capabilities provided by Intel Pentium processor manufactured by Intel Corporation, Santa Clara, Calif., is used. Other types of parallel processing or acceleration available on other types of processors can also be used. The MMX™ parallel processing instructions available in Pentium II, III and IV processors can be used. Furthermore, the SIMD™ and SSE™ parallel processing instructions available in Pentium III and IV can also be used. Moreover, the SSE2™ parallel processing instructions available in Pentium IV can also be used.

The translation and rotation corresponding to the optimal cost function is determined. Optimization includes minimization in the case of sum of absolute difference or maximization in the case of the correlation coefficient and the product of image intensities.

In the more general cases, gImage1 (100) and gImage2 (102) may correspond to the original image data themselves containing speckle, as opposed to the gradient data. In yet more general cases, gImage1 (100) and gImage2 (102) correspond to other types of feature images, such as ridges and images generated by filtering using a Laplacian of a Gaussian or other types of filters.

In order to speed the process of registration, the search for the optimum cost function is performed using a separable search paradigm. In FIG. 8, the two images, gImage1 (100) and gImage2 (102), respectively, corresponding to the same cardiac phase from the two clips, are searched in x-direction only and estimates a preliminary estimate for $t_x$ are determined in act 104. Using this $t_x$ as the starting point in act 106, a search in the y-direction only is performed and estimates a preliminary estimate for $t_y$ are determined. Using these $t_x$ and $t_y$ as the starting point in act 108, a search in θ only is performed and estimates a preliminary estimate for $t_{74}$ are determined. Using these $t_x$, $t_y$ and $t_\theta$, as the starting point in act 110, a search in x, y and θ all together is performed to obtain a finer estimate for $t_x$, $t_y$ and $t_\theta$.

Figure 9:
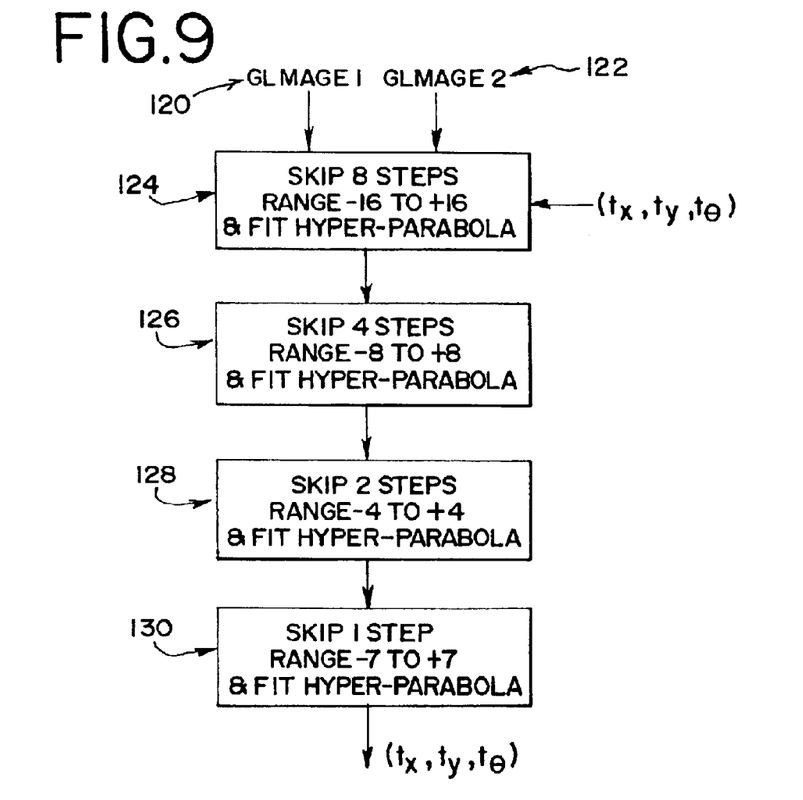

FIG. 9 elaborates act 110 further. In order to speed up the process of computing the optimal $t_x$, $t_y$ and $t_{74}$ even more, a hierarchical approach is taken. Two gradient images, gImage1 (120) and gImage2 (122), along with the preliminary estimates for $t_x$, $t_y$ and $t_{74}$ are used in act 124. The three search dimensions, x, y and θ are searched from −16 to +16 by skipping 8 units. In the case of x and y, a unit is a pixel and in the case of θ, a unit is a 1° angular increment. This corresponds to 5 points along each of the parameter dimensions, resulting in 5×5×5 points in the parameter space. Other units or different quanta or fractions of units may be used for each step. The cost function for each of the 5×5×5 points in the parameter space is computed and the point in the parameter space corresponding to the optimum cost function is selected.

The cost function typically takes the shape of a hyper-parabola, a parabola in 3-dimensions, near the global optimum. In order to converge at the global optimum of the cost function quickly, the hyper-parabola given by:

$$\Phi = ax^2 + by^2 + c\theta^2 + dxy + ey\theta + f\theta x + gx + hy + i\theta + j \quad (6)$$

is fit to the cost function, Φ, around a 5×5×5 neighborhood at the optimum to find the 10 coefficients, a, b, c, d, e, f, g, h, i and j, of a hyper-parabola. The fit is performed using a least squares fitting. Other types of functions and fittings may also be used and other sizes of neighborhoods may also be used. Once the 10 coefficients of the hyper-parabola are estimated, the optimum of the hyper-parabola corresponding to the global optimum of the cost function is computed. The coordinates of the optimum point in the parameter space are estimated using the coefficients of the hyper-parabola as given by:

$$\begin{bmatrix} x \\ y \\ \theta \end{bmatrix} = \begin{bmatrix} 2a & d & f \\ d & 2b & e \\ f & e & 2c \end{bmatrix}^{-1} \begin{bmatrix} g \\ h \\ i \end{bmatrix} \quad (7)$$

The results of estimating $t_x$, $t_y$ and $t_\theta$ and the two images, 120 and 122, are used in act 126. The above process is repeated by searching the parameter space from −8 to +8 with steps of 4. A hyper-parabola is again fitted to find a better estimate for $t_x$, $t_y$ and $t_{74}$. The results of estimating $t_x$, $t_y$ and $t_\theta$ and the two images, 120 and 122, are used in act 128. The above process is repeated by searching the parameter space from −4 to +4 with steps of 2. A hyper-parabola is again fitted to find a better estimate for $t_x$, $t_y$ and $t_\theta$. The results of estimating $t_x$, $t_y$ and $t_\theta$ and the two images, 120 and 122, are used in act 130. The above process is repeated by searching the parameter space from −7 to +7 with steps of 1. A hyper-parabola is again fitted to find a better estimate for $t_x$, $t_y$ and $t_\theta$. The process is now terminated and the values for $t_x$, $t_y$ and $t_\theta$ correspond to the translation and rotation between the two images, 120 and 122, and hence the two clips, 80 and 82.

Once the x- and y-translations, $t_x$ and $t_y$, and angular translation, $t_\theta$ parameters are estimated, the act 90 shown in FIG. 7 renders the results onto the display. Acts 84, 86, 88 and 90 or some combination thereof can be performed using a personal computer or a processor. The rendering is performed using a graphics accelerator card such as those manufactured by Nvidia Corporation, Santa Clara, Calif. Rendering is accomplished using an application programming interface, such as OpenGL. Other types of computers, graphics accelerators and application programming interfaces may also be used.

One or more options may be provided to the user to view the data from the two clips. In one embodiment, the user views a new clip generated by using the images from the two clips. Each image in the new clip is generated by compounding the corresponding images from the two input clips. In another embodiment, the user can view clip1 on the left hand side of the display and the clip2 on the right hand side of the display or vice versa. The boundary between the two clips can be moved from left to right and right to left using the mouse. In yet another embodiment, the data from clip1 are colored in one color, such as red, and the data from clip2 are colored in another color, such as blue. The data common to the two clips are colored using yet another color, such as white. Other tools for visualizing the data generated by combining clip1 and clip2 are also possible.

All of the processing, registration and rendering also includes 3D volume data as well. In this case, the two clips, clip1 (80) and clip2 (82) correspond to two sets of 3D volume data. The parameter space for correlation now includes x, y and z translations and α, β and θ rotations.

Referring again to FIG. 2, the temporal and spatial alignment acts 38 and 40 are performed simultaneously or subsequently. For example, a spatial-temporal alignment is performed by mathematical correlation of both spatial and temporal information. Other temporal and spatial alignment techniques are disclosed in U.S. application Ser. No. 09/369, 510, the disclosure of which is incorporated herein by reference.

Figure 5:
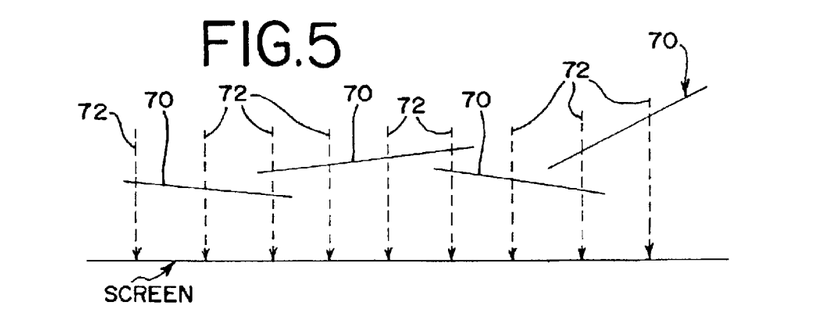
FIG. 5 is a graphical representation of one embodiment of rendering from two-dimensional images associated with similar but different planes.

The temporally and/or spatially aligned images are combined in act 42. For two-dimensional imaging, such as for an extended field of view image, the images, acquired through different acoustic windows, are either assumed to be coplanar or are aligned as a function of three dimensions as shown in FIG. 5. FIG. 5 shows a plurality of images 70 that overlap in two dimensions but are associated with different planes or positions in a third dimension. Ray lines 72 perpendicular to the screen are projected through the images 70. An extended field of view two-dimensional image is generated or volume rendered on a screen as a function of the data compounded along the ray lines 72.

In one embodiment, the images are combined by compounding. For example, an average or a weighted average is applied to the images. The weights applied in a weighed average may be selected as a function of the signal-to-noise ratio of each of the images, the phase of the physiological cycle represented by the images, the spatial position represented by the data or other variable. The compounding may also be a function of an amount of coherence of the first image with the second image. For each location within an image, a sum of data associated with that location is divided by the number of images contributing to the sum (i.e. the data is normalized as a function of the number of images). In other embodiments, the maximum or minimum value from both images associated with the same location is selected for imaging.

In one embodiment, the amount of compounding is selectable. For example, an amount of compounding between an average and selection of a maximum value is selected as a function of the application or the object being imaged. The weights for compounding are a Fermi-Dirac other function of the data for compounding, such as disclosed in U.S. Pat. No. 6,713,239, filed herewith, the disclosure of which is incorporated herein by reference.

The images are combined using pre-detected data or post-detected data. For example, a compound spectrum is provided by compounding images associated with different operating frequencies after detection. A synthetic spectrum is provided by combining data prior to detection. Likewise, a compound aperture is provided by combining images associated with different apertures, and a synthetic aperture is provided by combining images of detected data associated with different apertures prior to detection. The synthetic aperture reduces the speckle size of unresolvable targets and increases detail resolution of resolvable targets, or a compound aperture reduces speckle variants and improves detectability of directional targets for compounding two images associated with different acoustic windows. A sequential focus is provided by combining detected images associated with different transmit foci, and phase inversion may be provided by synthetic combination of pre-detected data.

In one embodiment, the two images are combined as a function of three-dimensional rendering. The images are positioned within three-dimensional space. Using ray lines, the volume is rendered by combining, such as compounding, the data from multiple images. FIG. 5 represents either two-dimensional volume rendering or three-dimensional volume rendering. In one example of three-dimensional volume rendering, the images 70 are positioned more vertically than horizontally as shown in FIG. 5 as a function or the acoustic window or placement of the transducer.

Figure 10:
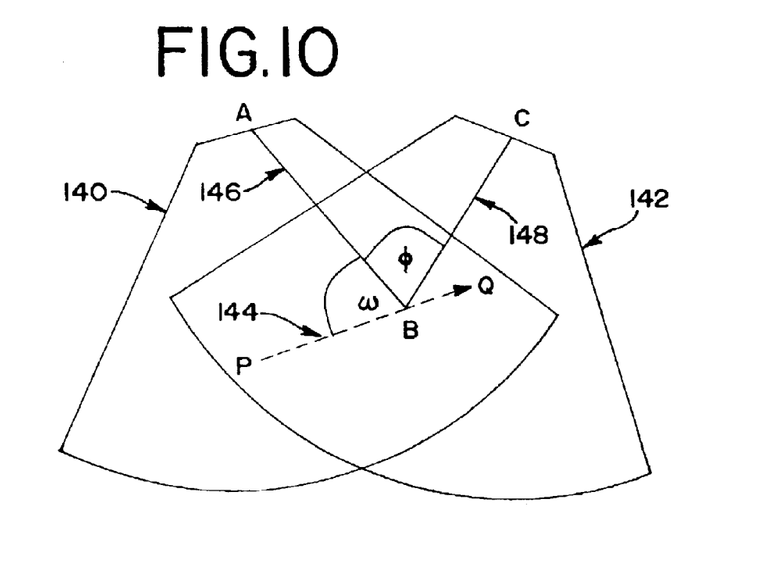
FIG. 10 is a graphical representation of an angular relationship in two scan planes.

In one embodiment, the images include B-mode data and Doppler data. Registration can be performed using B-mode data and rendering can be performed using both B-mode and Doppler data or using Doppler data alone. Since Doppler data is responsive to the angle of the scan line to the direction of flow, the data is angle-corrected prior to combination. FIG. 10 shows one embodiment. Two Doppler images, 140 and 142, corresponding to the two views are shown. Line PQ (144) denotes the direction of flow at point B. Point B is interrogated using ultrasound lines AB from image 140 and CB from image 148. Me angle made by the ultrasound line AB and the direction of flow is ω, while the angle made by the ultrasound line CB and the direction of flow is (ω+φ), where φ is the angle ABC. If the true velocity of flow at B is v, the estimate using line AB is $v_1 = v \cdot \cos(\omega)$, while the estimate using line CB is $v_2 = v \cdot \cos(\omega + \phi)$ Thus $v_1$ corresponds to the Doppler data in image 140 and $v_2$ corresponds to the Doppler data in image 142. Since angle φ is known from the registration act 88 above, both ω and v can be estimated from the estimate φ and the measurements, $v_1$ and $v_2$. There are several ways to do this and one way is shown in Equations 8 and 9 as follows:

$$\omega = \tan^{-1}\left[\frac{\cos\phi - \frac{v_2}{v_1}}{\sin\phi}\right] \quad (8)$$

$$v = \frac{v_1}{\cos\omega} \quad (9)$$

The displayed data can include v or ω both. In another embodiment, no angle correction is performed. Alternatively, any of various angle correction techniques can be used, such as those including automatically or manually determining the direction of flow In another embodiment, the Doppler angle is corrected in three dimensions by using three or more ultrasonic data sets containing different views of the object. In yet another embodiment, the Doppler angle from one view is transformed to the Doppler angle from another view.

While the invention has been described above by reference to various embodiments, it should be understood that many changes and modifications can be made without departing from the scope of the invention. For example, both dynamic and non-dynamic objects may be imaged. Spatial alignment may be used without temporal alignment and temporal alignment may be used without spatial alignment. Accordingly, object-phase synchronized imaging is provided separately from imaging using different acoustic images separated from an opaque barrier. Both techniques may be used in combination as well. As another example, the heart is imaged with an trans-esophageal probe from the esophagus. Images associated with different positions of the transducer array (i.e. different acoustic windows) may be separated by no opaque barrier, an aberration or a gas barrier. The images are aligned temporally and/or spatially for combination.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. A method for imaging the heart of a patient, the method comprising the acts of:

(a) acquiring a first set of images representing the heart during at least a portion of a first cardiac cycle, the first set acquired in response to a first imaging parameter;

(b) acquiring a second set of image representing the heart during a same portion of a subsequent cardiac cycle, the second set acquired in response to a second imaging parameter, the first set of images having a different spatial spectra than the second set of images based on the second imaging parameter being different than the first imaging parameter;

(c) temporally aligning images from the first set with images from the second set as a function of respective phases of the first and subsequent cardiac cycles; and (d) combining the temporally aligned images.

2. The method of claim 1 wherein (a) comprises acquiring the first set of images in response to a first acoustic window and (b) comprises acquiring the second set of images in response to a second acoustic window separated from the first acoustic window by a rib; further comprising;

(e) spatially aligning a first image from the first set with a second image from the second set prior to (d).

3. The method of claim 1 wherein (a) comprises acquiring in response to the first imaging parameter being a first center frequency, and (b) comprises acquiring in response to the second imaging parameter being a second center frequency different than a first center frequency.

4. The method of claim 1 wherein (a) comprises acquiring in response to the first imaging parameter being a first focal depth, and (b) comprises acquiring the second set of images in response to the second imaging parameter being a second focal depth different than a first focal depth; further comprising:
   (e) spatially aligning a first image from the first set with a second image from the second set prior to (d).

5. The method of claim 1 further comprising:
   (e) spatially aligning a first image from the first set with a second image from the second set as a function of correlation of the first image with the second image.

6. A method for ultrasonically imaging an object, the method comprising the acts of:
   (a) acquiring first and second sets of images representing an object, the first set of images acquired from a first acoustic window and the second set of images acquired from a second acoustic window separated from the first acoustic window by an opaque barrier, a transducer positioned adjacent to the opaque barrier for each of the first and second acoustic windows; and
   (b) combining a first image from the first set of images with a second image from the second set of images.

7. The method of claim 6 wherein (a) comprises acquiring the first and second images corresponding to a same phase within physiological cycles.

8. The method of claim 7 further comprising:
   (c) selecting the first and second images as a function of a signal representing the physiological cycle.

9. The method of claim 6 wherein (a) comprises acquiring the first image in response to a first spectrum and acquiring the second image in response to a second spectrum, the first spectrum at least partially not overlapping the second spectrum.

10. The method of claim 6 further comprising:
    (c) spatially aligning the first image with the second image.

11. The method of claim 10 wherein (c) comprises spatially aligning as a function of a gradient.

12. The method of claim 10 wherein (c) comprises spatially aligning as a function of correlation of the first image with the second image.

13. The method of claim 6 wherein (b) comprises volume rending as a function of the first and second images.

14. The method of claim 6 wherein (b) comprises combining prior to amplitude detection.

15. The method of claim 6 wherein (0) comprises combining after amplitude detection.

16. The method of claim 15 where the combining is after log compression.

17. The method of claim 6 wherein (b) comprises combining at each location in a field of view as a function of a number of frames associated with the respective location.

18. The method of claim 6 wherein (a) comprises acquiring the first image and the second image wherein the firs acoustic window is separated from the second acoustic window by bone.

19. The method of claim 6 further comprising:
    (c) transforming a Doppler angle for the first image to a Doppler angle for the second image.

20. The method of claim 6 wherein (a) comprises acquiring the first image and the second image wherein the first acoustic window is separated from the second acoustic window by gas.

21. A system for acquiring imaging data representing an object, the system comprising:
   a receive beamformer operable to acquire first and second sets of images representing an object, the first set of images responsive to a first acoustic window and the second set of images responsive to a second acoustic window separated from the first acoustic window by an opaque barrier;
   a transducer connected with the receive beamformer, the transducer positionable adjacent to the opaque barrier at each of the first and second acoustic windows; and
   a first processor operable to combine a first image of the first set of images with a second image of the second set of images.

22. The system of claim 21 further comprising a second processor operable to associate a temporal designator indicating a phase within a physiological cycle to the first and second images, the first and second images designated with a same period of the physiological cycle.

23. The system of claim 21 further comprising a transmit beamformer wherein the receive beamformer is responsive to echo signals generated by the transmit beamformer and wherein the first image is responsive to a fist spectrum and the second image is responsive to a second spectrum, the first spectrum different than the first spectrum, the first specimen at least partially not overlapping the second spectrum.

24. The system of claim 21 wherein the first processor is operable to spatially aligning the first image with the second image.

25. The system of claim 21 wherein the first processor is operable to combine the first image with the second image.

26. A method for acquiring data for imaging a dynamic object, the method comprising the acts of:
    (a) acquiring a first set of images representing an object during at least a portion of a physiological cycle, the first set acquired in response to a first imaging parameter;
    (b) acquiring a second set of image representing the object during a same portion of a subsequent physiological cycle, the second set acquired in response to a second imaging parameter, the second imaging parameter different than the first imaging parameter;
    (c) temporally aligning images from the first set with images from the second set as a function of respective phases of the physiological cycle; and
    (d) combining the temporally aligned images.

27. The method of claim 26 wherein (a) comprises acquiring the fist set of images in response to a first acoustic window and (b) comprises acquiring the second set of images in response to a second acoustic window separated from the first acoustic window by an opaque barrier.

28. The method of claim 26 wherein (d) comprises combining a first image from the first set with a second image from the second set before detection.

29. The method of claim 26 wherein (d) comprises combining a first image from the first set with a second image from the second set after detection.

30. The method of claim 26 wherein (a) comprises acquiring in response to the first imaging parameter being a first center frequency, and (b) comprises acquiring in response to the second imaging parameter being a second center frequency different than a first center frequency.

31. The method of claim 26 wherein (a) comprises acquiring in response to the first imaging parameter being a first bandwidth, and (b) comprises acquiring the second set of images in response to the second imaging parameter being a second bandwidth different than a first bandwidth.

32. The method of claim 26 wherein (a) comprises acquiring in response to the first imaging parameter being a first transmit and/or receive aperture, and (b) comprises acquiring the second set of images in response to the second imaging parameter being a second transmit and/or receive aperture different than a first transmit and/or receive aperture.

33. The method of claim 26 wherein (a) comprises acquiring in response to the first imaging parameter being a first focal depths and (b) comprises acquiring the second set of images in response to the second imaging parameter being a second focal depth different than a first focal depth.

34. The method of claim 26 wherein (a) comprises acquiring in response to the first imaging parameter being a first filter response, and (b) comprises acquiring the second set of images in response to the second imaging parameter being a second filter response different than a first filter response.

35. The method of claim 26 wherein (c) comprises temporally aligning in response to all ECG signal.

36. The method of claim 26 wherein (c) comprises temporally aligning as a function of Doppler data.

37. The method of claim 26 further comprising:
 (e) spatially aligning a first image from the first set with a second image from the second set as a function of correlation of the fast image with the second image.

38. The method of claim 26 wherein (d) comprises combining as a weighted average.

39. An ultrasound system for acquiring data for imaging a dynamic object, the system comprising:
 a transmit beamformer;
 a receive beamformer for acquiring first and second sets of images representing an object during a portion of physiological cycles, the first set acquired in response to a first imaging parameter and transmissions from the transmit beamformer, the second set acquired in response to a second imaging parameter, the second imaging parameter different than the first imaging parameter;
 a first processor operable to temporally align images from the first set with images from the second set as a function of respective phases of the physiological cycle; and
 one of a second processor and the first processor operable to combine the temporally aligned images.

40. The system of claim 39 further comprising a transducer connected with the transmit and receive beamformers wherein the first set of images are responsive to a first acoustic window as a function of a first aperture of the transducer and the second set of images are responsive to a second acoustic window separated from the first acoustic window by an opaque barrier, the second acoustic window a function of a second aperture of the transducer.

41. The system of claim 39 further comprising a detector connected with a combined data output of the first processor.

42. The system of claim 39 further comprising a detector connected between the receive beamformer and the second processor, the second processor operable on detected data.

43. The system of claim 39 wherein the transmit and receive beamformers operate at a first center frequency for acquiring the first set and a second, different center frequency for acquiring the second set.

44. The system of claim 39 wherein the first imaging parameter is a first bandwidth, and the second imaging parameter is a second bandwidth different than a first bandwidth.

45. The system of claim 39 wherein the first imaging parameter is a first transmit and/or receive aperture, and the second imaging parameter is a second transmit and/or receive aperture different than a first transmit and/or receive aperture.

46. The system of claim 39 wherein the first imaging parameter is a first focal depth, and the second imaging parameter is a second focal depth different than a first focal depth.

47. The system of claim 39 further comprising a filter connected with the receive beamformer wherein the first imaging parameter is a first filter response, and the second imaging parameter is a second filter response different than a first filter response.

48. The system of claim 39 further comprising a ECG input connected with the first processor, wherein the first processor is operable to temporally align in response to an ECG signal from the ECG input.

49. The system of claim 39 wherein the first processor is operable to temporally align as a function of Doppler data.

50. The system of claim 39 wherein the first processor is operable to spatially aligning a first image from the first set with a second image from the second set as a function of correlation of the first image with the second image.

51. The system of claim 39 wherein the second processor is operable to compound a first image with a second image as a weighted average.

* * * * *